(12) United States Patent
Taylor

(10) Patent No.: US 6,605,214 B1
(45) Date of Patent: Aug. 12, 2003

(54) DEVICES FOR PREPARING HEMODIALYSIS SOLUTIONS

(75) Inventor: Michael A. Taylor, Napa, CA (US)

(73) Assignee: Prismedical Corporation, Napa, CA (US)

(*) Notice: Subject to any disclaimer, the term of this patent is extended or adjusted under 35 U.S.C. 154(b) by 0 days.

(21) Appl. No.: 09/518,482

(22) Filed: Mar. 3, 2000

Related U.S. Application Data

(60) Provisional application No. 60/122,510, filed on Mar. 3, 1999.

(51) Int. Cl.[7] .............................................. B01D 61/00
(52) U.S. Cl. .................. 210/232; 210/257.1; 210/259; 210/283; 210/284; 210/290; 210/291; 422/102; 422/255; 422/261; 604/221; 604/416
(58) Field of Search .................. 210/647, 232, 210/257.1, 259, 283, 284, 290, 291; 604/84, 410, 416, 221; 422/102, 255, 261

(56) References Cited

U.S. PATENT DOCUMENTS

| | | | |
|---|---|---|---|
| 4,467,588 A | 8/1984 | Carveth | 604/410 |
| 4,548,606 A | 10/1985 | Larkin | 604/414 |
| 4,756,838 A | 7/1988 | Veltman | 210/646 |
| 4,784,495 A | 11/1988 | Johnsson et al. | 366/160 |
| 4,871,463 A | 10/1989 | Taylor et al. | 210/161 |
| 5,071,558 A | 12/1991 | Itob | 210/647 |
| 5,122,516 A | 6/1992 | Watanabe et al. | 210/646 |
| 5,259,954 A | 11/1993 | Taylor | 210/232 |
| 5,344,231 A | 9/1994 | Jönsson et al. | 604/84 |
| 5,395,323 A | 3/1995 | Berglund | 604/84 |
| 5,511,875 A | 4/1996 | Jönsson et al. | 366/136 |
| 5,725,777 A | 3/1998 | Taylor | 210/232 |

OTHER PUBLICATIONS

Vlchek, D.L., et al. (1992) Water Quality for dialysis, 2nd edition. current convepts in hemodialyzer reprocessing. AAMI Dialysis Monograph Series. 7 pages.

Primary Examiner—John Kim
(74) Attorney, Agent, or Firm—Knobbe,. Martens, Olson & Bear, LLC

(57) ABSTRACT

A single housing includes a diluent inlet, a solution outlet, and a plurality of discrete reagent beds comprising at least one reagent in dry form, wherein the reagent is present in the discrete reagent bed in a proportion sufficient for production of a complete hemodialysate solution.

26 Claims, 4 Drawing Sheets

DEVICES FOR PREPARING HEMODIALYSIS SOLUTIONS

REFERENCE TO RELATED APPLICATIONS

This application claims priority under 35 U.S.C. §119(e) to U.S. Provisional Patent Application No. 60/122,510, entitled "Methods and Devices for Preparation Hemodialysis Solutions," filed Mar. 3, 1999.

FIELD OF THE INVENTION

This invention relates generally to devices for preparing solutions from dry reagent constituents and, more particularly, to the preparation of solutions suited for hemodialysis.

BACKGROUND OF THE INVENTION

Patients with sufficiently impaired kidney function are required to undergo dialysis to remove toxins from their blood. In general, dialysis involves the removal of toxins from body fluids by diffusing the toxins across a permeable membrane into a toxin-free dialysis solution. In the case of hemodialysis, blood is removed from a patient's body and purified of toxins externally in a dialysis machine. After removal of the toxins, the purified blood is returned to the patient.

Patients receiving hemodialysis typically utilize 75 to 150 liters of prepared dialysis solution three times a week. The largest ingredient in these solutions is water. Reducing water in the dialysis solutions thus reduces the amount of solution which needs to be stored or transported.

Dialysis solutions are currently prepared from separate concentrated solutions. For example, one concentrate, Preparation A, includes a mixture of varied salts, sugars and acids dissolved in water. Another concentrate, Preparation B, is made of sodium bicarbonate dissolved in water. The constituents must be kept separate until soon before hemodialysis because of the tendency for insoluble precipitates to form in the combined solution. As one example, sodium bicarbonate in the presence of various calcium salts, in dry or liquid form, will precipitate calcium carbonate. Typically, these two concentrates are shipped and stored separately in 200 liter drums. When it comes time for administering the hemodialysis to a patient, the concentrates are mixed together in a ratio of 4 liters of Preparation A to 6 liters of Preparation B, along with 110 liters of diluent water. The employment of concentrates speeds and simplifies mixing on site, e.g., in a hospital, relative to time-consuming and complicated dissolution conventionally performed by the concentrate providers.

On the other hand, even in concentrated solutions, the Preparations A and B are themselves bulky and difficult to transport. Moreover, bicarbonate solutions such as Preparation B have a tendency to form carbon dioxide and alter the pH of their solution over extended periods of time, even if not mixed with other reagents. Another logistical problem with preparing dialysis solutions is the need to keep the solutions sterile and endotoxin free.

Various attempts have been made to minimize the logistics required to prepare dialysis solutions. Complete systems have been developed for separating incompatible reagents, water pumping and recirculation systems, pH and conductivity monitors, and water heating components (U.S. Pat. Nos. 5,511,875 & 5,344,231, 4,784,495). In these systems, dissolution is controlled by recirculation of diluent through separate containers of dry powders or acids to form concentrates, which are in turn mixed mechanically to achieve the appropriate concentration. Elaborate mechanisms are used for routing fluids, measuring concentrations and heating prepared solutions.

Other means of preparing dialysate solutions have included systems for mechanically crushing reagents to fine powders and then vaporizing water in the presence of the finely divided, recycled particles (U.S. Pat. No. 4,756,838).

Dialysate solution preparation systems have also packaged together sterile water and powder reagents, separated by a frangible barrier between the compartments. In order to use the solution, the barrier is broken so that the reagents and water can mix together (U.S. Pat. Nos. 4,467,588 and 4,548,606).

Others have also attempted to enhance dissolution of dry reagent formulations by modifying the formulation of the dialysis solution in an attempt to minimize the formation of insoluble precipitates (U.S. Pat. No. 5,122,516).

Significant logistical problems are associated with prior art methods and devices for providing hemodialysis solutions. In addition to reactivity among the constituents of the solutions, transportation of liquid hemodialysis solutions is costly and awkward.

The invention disclosed herein solves these problems and provides tremendous advantages over prior systems.

SUMMARY OF THE INVENTION

One embodiment of the disclosed invention relates to a single housing having a diluent inlet and a solution outlet, the housing containing a compression component and at least one reagent bed comprising dry reagent in amounts and proportions sufficient for production of a complete dialysis solution.

Another embodiment relates to a system for providing hemodialysis solution, comprising a water purification pack, and a dry reagent module configured to connect downstream of the water purification pack, wherein the reagent module comprises a housing, a diluent inlet, a solution outlet, at least one compression component, and reagents in an amount and proportion sufficient for production of a complete hemodialysis solution.

Another embodiment of the disclosed invention relates to a method for producing a dialysate solution, comprising passing diluent through a dry reagent bed, thereby consuming reagents in the bed, carrying the consumed reagents with the diluent out of the bed, and compacting the reagent bed as the reagents are consumed.

Still another embodiment relates to a device storing and delivering dry reagents for medical fluids, comprising a single housing with a diluent inlet and a solution outlet, the housing containing a compression component and at least two discrete reagent beds.

DETAILED DESCRIPTION OF PREFERRED THE EMBODIMENTS

Figure 1:
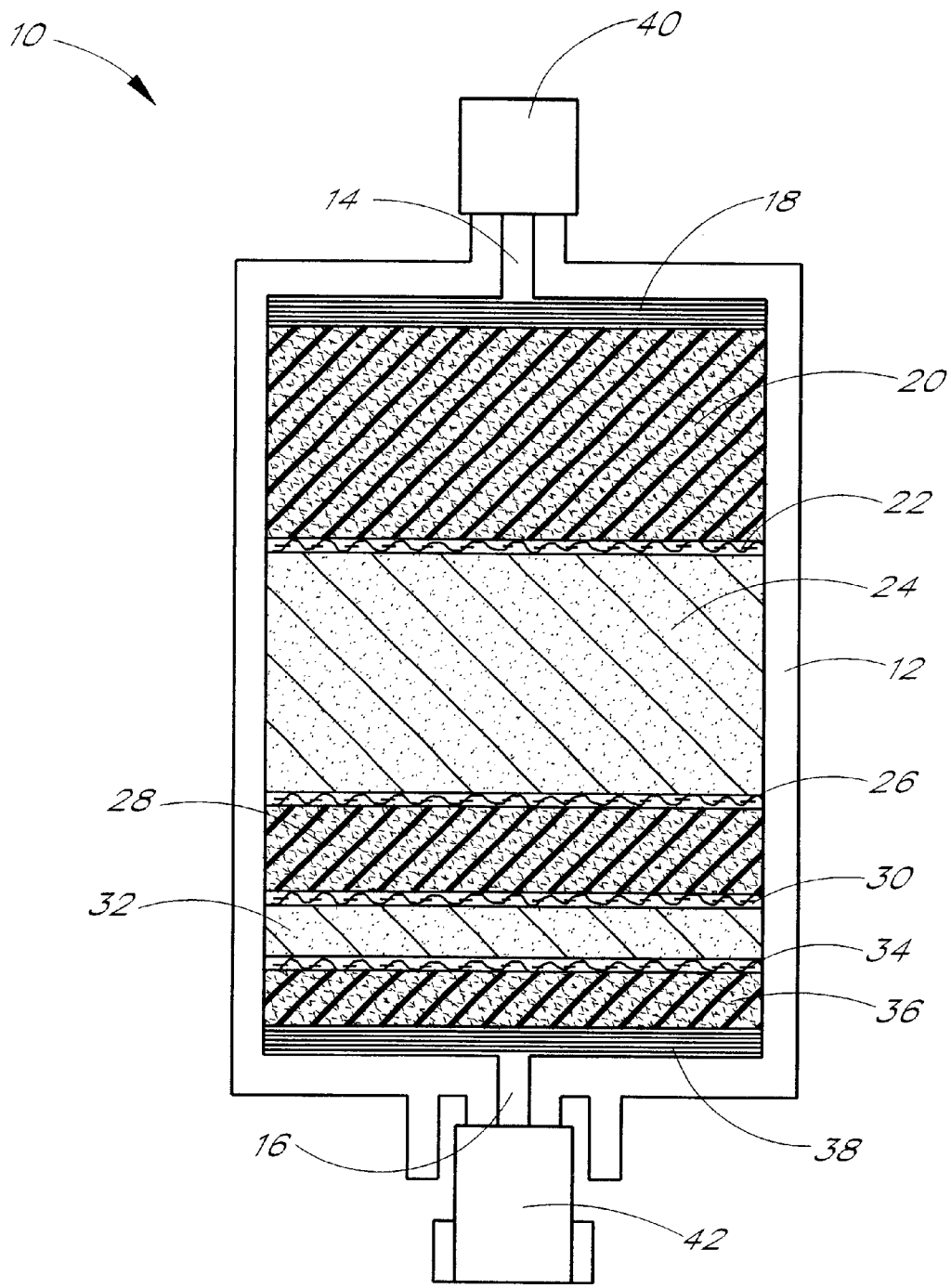
FIG. 1 is a schematic cross-section of a hemodialysate delivery pack, constructed in accordance with a preferred embodiment of the invention.

While the illustrated embodiments are described in the context of hemodialysate solutions, the skilled artisan will find application for principles disclosed herein in a variety of contexts, particularly where dissolution of multiple reagents is desired. Moreover, the invention has particular utility where the reagents react with one another and/or are unstable in solution.

The disclosed embodiments provide a device for producing a liquid hemodialysis solution from dry formulations of reagents stored in a self-contained device. The methods and devices described herein enable storage and transportation of dry formulations of reagents that are used to produce a hemodialysate. Advantageously, dry reagent storage and transportation provides the ability to minimize the effects of pH changes due to the formation of carbon dioxide that result from the combination of sodium bicarbonate and various acids and dissociable salts when liquid dialysates are stored for long periods of time.

Moreover, the described embodiments also provide purification of water available at a remote location, in order to produce a sterile dialysate solution. In combination with the provision of dry forms of reagents, on-site water purification allows one to transport the essential ingredients of hemodialysis solutions without transporting the diluent for the solution, thus removing between 95% to 99% of the weight of the prepared solution. This provides a tremendous advantage over prior systems.

The disclosed embodiments also provide a closed device that enables the maintenance of sterility of the constituents up to and during production of a solution therefrom. The embodiments further provide a device that allows the user to observe the dissolution of the contained reagent formulations to assure that the reagents are completely placed into solution and that no insoluble precipitates have formed within the device and remain within the housing after the soluble reagents have been dissolved. The device also simplifies the containment and mixing of incompatible dry reagents in preparing solutions for injection into patients.

The disclosed embodiments also provide an economical device that can manually produce a liquid hemodialysate, and that can operate without the aid of complex mechanical or electrical assistance. A system is provided for containing incompatible reagents within a single housing. Such reagents would, if allowed to contact one another, even in dry form, create insoluble precipitates. The device contains dry reagent formulations and is configured to restrain movement of particles, thus reducing the risk of mixing incompatible reagents within the device.

The disclosed embodiments also provide an attachment for the dialysis delivery device that purifies potable water to the standards set by the AAMI for water to be used in dialysis solution preparations.

The device of the illustrated embodiment is designed for one-time use. Nevertheless, the skilled artisan will readily appreciate from the disclosure herein that a re-usable devices can function in a similar manner, by provision of a re-fillable and re-sealable housing.

The size of the device depends upon the dry volume of the reagent formulation. In one embodiment, the size of the reagent housing is from about 6 inches (15.24 cm) to about 24 inches (60.96 cm) in height and from about 1 inch (2.54 cm) to about 12 inches (30.48cm) in diameter. The housing preferably has rigid walls with an axial inlet and an outlet.

When the inlet and outlet ports are covered, the system is sufficiently closed to prevent gross transfer of water vapor into the device. In addition, the covers prevent the release of formulation particles.

Within the housing, the reagents are confined in beds between controlled porous restraints, and are compressed axially by compressive components to minimize the interstitial spaces between reagent particles. The illustrated device advantageously contains no moving parts. To prevent formation of insoluble precipitates within the device, the constituents of one bed (e.g., calcium chloride), are separated from incompatible reagents (e.g., sodium bicarbonate) within the housing. Thus, in the illustrated embodiment, calcium chloride is enclosed within a separate layer comprising a porous bed restraint and compression component.

Additionally, in one embodiment, a water purification pack is attached to the hemodialysis delivery pack, enabling purification of non-sterile water. Purified water is thus provided on-site for dissolving and reconstituting the dry dialysis reagent formulations, such that sterilized water need not be separately stored or transported. Rather, available water, such as municipal or "tap" water, can be utilized in conjunction with the dry reagent cartridge.

By facilitating dissolution of the dry reagents with purified water immediately prior to administration to the patient, the preferred embodiments thus minimize the risk of forming precipitates when the liquid dialysate is stored for extended periods of time. The risk of pH variation, associated with formation of carbon dioxide, is similarly minimized by the provision of on-site dissolution.

APPARATUS FOR PREPARING HEMODIALYSIS SOLUTION

Reagent Container

Figure 2:
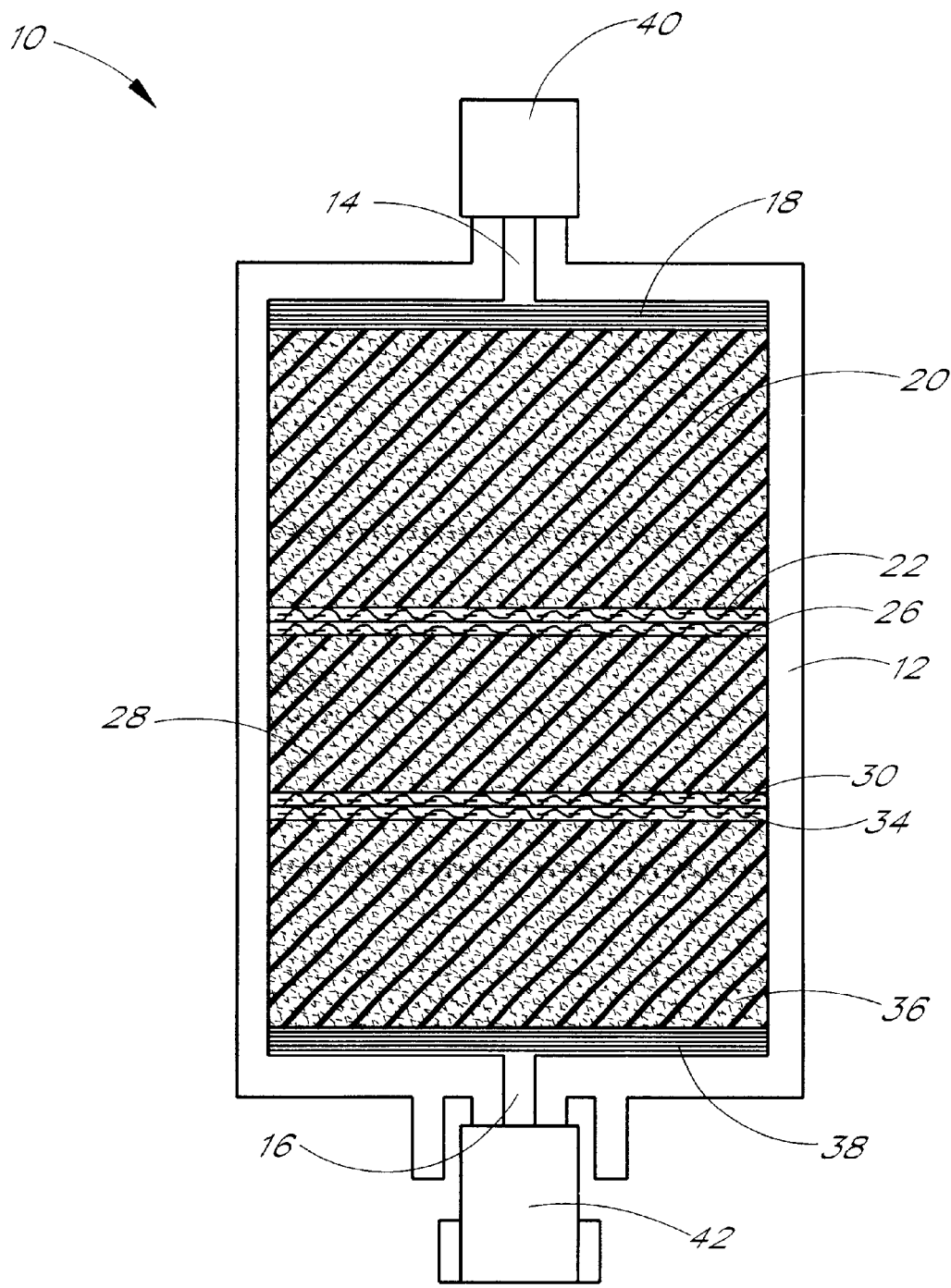
FIG. 2 illustrates the hemodialysate delivery pack of FIG. 1 following reagent dissolution.

FIGS. 1 and 2 illustrate a system 10 for preparing hemodialysate solutions. The illustrated embodiment comprises a rigid walled housing 12 with a terminal inlet port 14 opposite a terminal outlet port 16. The housing 12 is preferably transparent or translucent, advantageously enabling the user to observe the dissolution as diluent passes through the reagent bed. Examples of transluent and transparent polymers are polypropylene, polycarbonate and many other well known materials. Additionally, using transparent or translucent polymers in the housing 12 enables the user to observe the presence of insoluble precipitates within the reagent bed (if present) prior to introducing the prepared hemodialysate solution to a dialysis machine hooked to a patient.

Within the housing, adjacent to the inlets is an inlet frit 18, which serves as a safety filter to contain any reagent which escapes the restraints described below. The inlet flit 18 preferably comprises a porous element having a porosity smaller than the smallest particle of the reagents housed within housing. The porous element can be identical in structure to the restraints described below. The fits thus serve as filters to ensure that no reagent escapes the housing or cartridge 12 prior to dissolution, as will be described below. An exemplary frit 18 is a multilayered polypropylene laminate, having a porosity between about 1 $\mu$m and 100 $\mu$m, more preferably between about 10 $\mu$m to 50 $\mu$m. Further details on the preferred material are given below, with respect to the reagent restraints.

Immediately axial to the inlet frit 18 is an upstream or first reagent compression component 20. The compression components preferably comprise materials that have sponge-like elasticity and, as a result of compression, exert axial pressure while trying to return to its original, expanded form.

The compression components preferably comprise compressible, porous, open cell polymer or foam, desirably more porous than the frits, to avoid generation of back pressure. An exemplary material for the compression component is a polyurethane foam. Desirably, the compression components exert a compressive force on the reagent bed regardless of the size of the reagent bed. In other words, the compression components would, if left uncompressed, together occupy a greater volume than that defined by the housing 12. Desirably, the pressure exerted is between about 50 psi and 500 psi, more preferably between about 100 psi and 300 psi.

Downstream of the reagent compression component 20 is a primary reagent bed upstream restraint 22, which restrains a primary reagent bed 24 at the upstream end. At the opposite or downstream end of the primary reagent bed 24 is a primary reagent bed downstream restraint 26. Downstream of the primary reagent bed downstream restraint 26 is a second compressive component 28. Downstream of the second compressive component 28 is a secondary reagent upstream restraint 30. This component restrains a secondary reagent bed 32. Downstream of the secondary reagent bed 32 is a secondary reagent downstream restraint 34. At the outlet terminal of the secondary reagent downstream restraint 34 is a third compressive component 36. At the outlet end of the third compressive component 36 is an outlet frit 38, adjacent the housing outlet port 16. The housing inlet 14 and outlet 16 are covered by the inlet port cover 40 and the outlet port cover 42, respectively.

Accordingly, the primary reagent bed 24 is confined between the upstream and downstream restraints 22, 26, while the secondary reagent bed 32 is similarly confined between upstream and downstream restraints 30, 34. The reagent bed restraints 22, 26, 30 and 34 are preferably composed of a layer of woven or non-woven materials, sintered polymers or porous sheets which provide the desired porosity. Such restraints can be made hydrophobic or hydrophilic, as suitable for different formulations of reagents.

The reagent bed restraints 22, 26, 30 and 34 prevent the passage of reagent particles in their dry formulation. The porosity of the restraints is therefore selected to be less than the size of the smallest particles within the reagent bed, depending upon the particular reagent formulations and physical particle size desired. Desirably, the pores are large enough to avoid excessive pressure drop across the restraints. Preferably, the restraint porosity in the range between about 1 µm and 100 µm, more preferably between about 10 µm to 50 µm. An exemplary restraint, suitable for the illustrated hemodialysis application, comprises a non-woven polymer, particularly polypropylene with a porosity of about 20 microns. Another exemplary restraint comprises sintered polyethylene with a porosity of about 30 microns.

The compressive components 20, 28 and 36 are formed of materials which have sponge-like elasticity and, as a result of compression, exert axial pressure while trying to return to its original, expanded form. The compressive components 20, 28 and 36 preferably comprise compressible, porous (open cell) polymers, desirably more porous than the restraints and frits, to avoid generation of back pressure. It will be understood that, in other arrangements, metal or polymer springs and porous plates can serve the same function. Alternative compression components are disclosed, for example, with respect to FIGS. 12–15; Col. 9, lines 8–53 of U.S. Pat. No. 5,725,777, the disclosure of which is incorporated herein by reference. It will also be understood, in view of the discussion below, that a single compression component can serve the function of the illustrated three compression components, and that two, four or more can also be employed if desired.

In the illustrated embodiment, a complete formulation of the dry reagents required to produce a hemodialysis solution is provided within the housing 12. These dry formulations typically contain reagents that form insoluble precipitates when exposed to each other for prolonged periods of time in either dry or liquid forms. One example of this type of incompatible reagents is sodium bicarbonate and calcium chloride, which react to form insoluble, calcium carbonate. Because of the potential reactivity of incompatible reagents, it is preferable to separately store these reagents within the device housing 12.

This is accomplished by separating reagents into compatible groupings, which are then placed in separate compartments within the housing. The compartments are represented by the primary 24 and secondary 32 reagent beds in the illustrated embodiment. The potentially reactive reagents are thereby constrained from movement through the device by reagent bed restraints 22, 26, 30 and 34 at the upstream and downstream ends of each of the reagent beds 24 and 32. As noted above, the reagent bed restraints 22, 26, 30 and 34 prevent the passage of reagent particles in their dry form.

In the illustrated embodiment, the primary reagent bed 24 is a reagent mixture, preferably comprising: a bicarbonate, such as sodium bicarbonate; electrolytes, such as sodium chloride, magnesium chloride, potassium chloride, dextrose, and sodium acetate; and an acid, such as citric acid.

The secondary reagent bed 32 contains at least one component which is unstable in the presence of at least one component in the primary reagent bed. In the illustrated embodiment, the secondary reagent bed 32 contains calcium chloride. The skilled artisan will readily appreciate that, in other arrangements, the primary reagent bed 24 can contain the calcium chloride if the secondary reagent bed contains the bicarbonate. Other incompatible reagents for medical solutions can be similarly separated in alternative embodiments. Moreover, three or more reagent beds can be utilized to separate multiple incompatible reagents.

The illustrated housing 12 holds reagents sufficient to produce 120 L of a typical hemodialysate solution. Accordingly, the reagent beds hold the following reagents:

|  | Mass (g) | g/L |
|---|---|---|
| Primary Reagent Bed |  |  |
| Calcium chloride, dihydrate | 25.9 | 0.2 |
| Magnesium chloride, hexahydrate | 9.1 | 0.1 |
| Citric acid, anhydrous | 18.7 | 0.2 |
| Sodium acetate, trihydrate | 7.0 | 0.1 |
| Sodium chloride | 695.2 | 5.8 |
| Dextrose | 240.0 | 2.0 |
| Subtotal Grams of Agents | 995.8 | 8.3 |
| Secondary Reagent Bed |  |  |
| Sodium bicarbonate | 216.7 | 1.8 |
| Total Grams of Agents | 1212.5 | 10.1 |

The dry volume of the above-listed reagents, which can produce 120 L of 0.2% dextrose hemodialysate, is about 890 mL. If a smaller or larger volume of solution is desired, the skilled artisan can readily determine the proportionate weight and volume of dry reagents required in the reagent beds 24, 32.

The reagents in the first and second beds can be present in various ratios. The range of ratios for the components present in the reagent beds are from about 0.1:100 to about 100:0.1 measured in grams per liter (g/L). In one embodiment, the ratios of the reagent bed component ratios range from about 0.5:100 to about 100:0.5 measured in grams per liter (g/L). In another embodiment the reagent bed component ratios range from about 0.7:10 to about 10:0.7 measured in grams per liter (g/L). In still another embodiment, the reagent bed component ratios range from about 1:1 measured in grams per liter (g/L). In one particular embodiment the components of the reagent beds are present in ratios of about 1:1.2 measured in grams per liter (g/L).

Water Purification Pack

Figure 3:
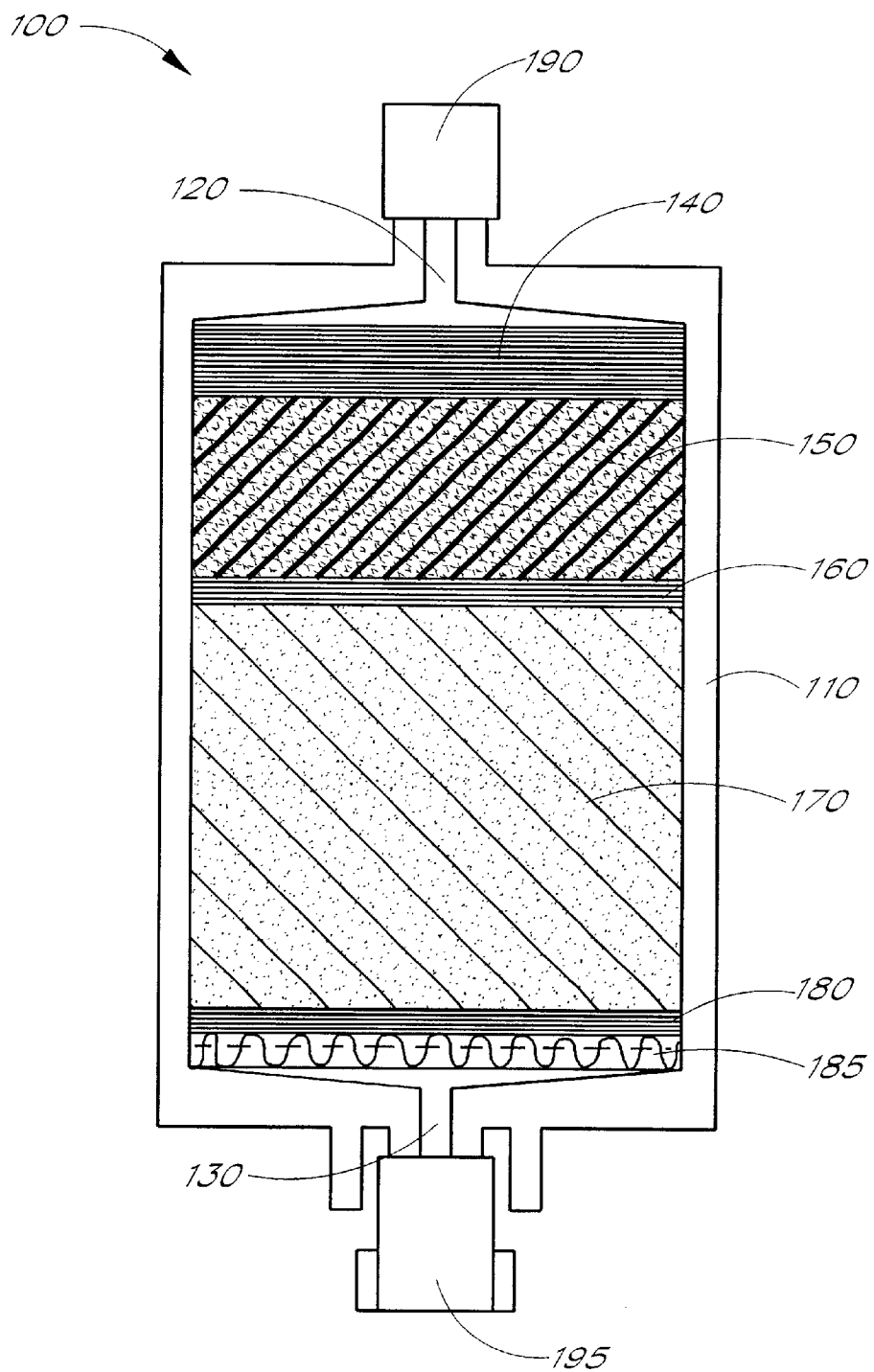
FIG. 3 is a schematic cross-section of a water purification pack, constructed in accordance with the preferred embodiment.

Referring to FIG. 3, a water purification pack is optionally provided for simultaneous purification of water to the quality required for dialysis applications. Advantageously, available water (e.g., tap water) can be introduced to the system, purification is conducted through the purification pack, and dialysate solution is produced. Accordingly, storage of bulky purified water and complex machinery for purifying water is obviated.

In the past, purifying non-sterile water to the quality standards suitable for use as a diluent for introduction into humans and other subjects required extensive mechanical filtration, pumping, distribution, and monitoring systems. These problems are eliminated in one embodiment of the disclosed invention by purifying water through the purification pack of FIG. 3. This compact, lightweight pack is capable of water purification at the point of administration in compliance with the standards set by the Association for the Advancement of Medical Instrumentation (AAMI) for dialysis water (Water Quality for Dialysis, $2^{nd}$ Edition, AAMI WQD, 1993.) These standards are listed below:

AAMI Standards for Hemodialysis Water Quality:

Microbiological Monitoring

Should be performed at least monthly

Total viable microbial counts shall not exceed 200/mL in water used to prepare dialysate, or 2000/mL in proportioned dialysate exiting the dialyzer.

Chemical Contaminants Monitoring

Should be performed at least yearly if prepared by DI or RO, more frequently if prepared with lesser level of treatment.

AAMI maximum levels of chemical contaminants*:

| Contaminant | Suggested Maximum Level (mg/L) |
|---|---|
| Calcium | 2 (0.1 mEq/L) |
| Magnesium | 4 (0.3 mEq/L) |
| Sodium** | 70 (3 mEq/L) |
| Potassium | 8 (0.2 mEq/L) |
| Fluoride | 0.2 |
| Chlorine | 0.5 |
| Chloramines | 0.1 |
| Nitrate (N) | 2 |
| Sulfate | 100 |
| Copper, Barium, Zinc | 0.1 each |
| Aluminum | 0.01 |
| Arsenic, Lead, Silver | 0.005 each |
| Cadmium | 0.001 |
| Chromium | 0.014 |
| Selenium | 0.09 |
| Mercury | 0.0002 |

*The physician has ultimate responsibility for determining the quality of water used for dialysis.
**230 mg/L (1 0 mEq/L) where sodium concentration of the concentrate has been reduced to compensate for the excess sodium in the water, as long as conductivity of water is being continuously monitored.

The above standards represent a summary of the water quality provisions of AAMI (1993), as published in the FDA's *Quality Assurance Guidelines for Hemodialysis Devices* (Vlchek et al., 1992), the disclosure of which is incorporated herein by reference.

In the illustrated embodiment, the water purification pack comprises a housing 110 with an axial inlet 120 and an outlet 130. Immediately downstream of the housing inlet 120 is a depth filter 140. The depth filter 140 retains insoluble particulates and microbes greater than the pore size of this component. The porosity of the illustrated depth filter 140 is preferably from 1 to 10 microns. Preferred materials for this component include primarily cellulose-based materials or plastic polymers. The depth filter 140 is preferably formed in multiple layers, and in one embodiment the depth filter comprises 2–3 layers of material. Alternatively, commercially available cellulose-based depth filters can be employed, as will be understood by one of ordinary skill in the art.

Downstream of the depth filter 140 is a bed of granular carbon 150. This component provides a means of removing residual organic contaminants, including commonly used additives placed in the municipally treated waters to minimize microbial growth (for example, chlorine, trihalomethanes and chloramine).

Adjacent to the downstream end of the granular carbon bed 150 is a carbon bed restraint 160. The restraint 160 is a filter of controlled porosity, preferably comprising cellulose-based materials or plastic polymers having a pore size down to about 1 micron. This component prevents passage of particulates shed by the granular carbon bed 150, as well as providing a secondary assurance that insoluble particulates do not pass further through the water purification pack 100.

Adjacent to the downstream side of the carbon bed restraint 160 is a bed of deionization resin beads 170. The resin bed comprises a mixture of pharmaceutical grade resins with strong anion exchanger and cation exchanger chemistries. This component serves to retain dissociable ions and other charged dissolved solids within the water as it passes through the deionization bed 170. Such resins are available, for example, from Rohm & Hass (Philadelphia, P. under the trade name IRN 150 or from Sybron (Birmingham, N.J. under the trade name NM60). The resin bed also retains endotoxins that escape the upstream filtration components.

Downstream of the deionization resin bed 170 is a deionization bed restraint 180 and a terminal filter element 185, in sequence. The restraint 180 is preferably a rigid or pliable disc of porous material separating the deionization bed 170 and the terminal filter element 185, and can be as described above with respect to the carbon bed restraint 160. The resin bed restraint 180 serves to prevent passage of deionization bed fragments or fines as well as any other particulates that reach this layer. The restraint also serves to protect the filter element 185 downstream of the restraint 180.

The terminal filter element 185 of the illustrated embodiment is a 0.2 micron or finer filter composed primarily of nylon or plastic polymers. The terminal filter may optionally be treated to incorporate one or more quaternary amine exchangers for binding endotoxins. Alternatively, the terminal filter can comprise a 0.2 micron or finer filter along with a second membrane that has enhanced endotoxin binding characteristics. Such endotoxin binding membranes are commercially available under the trade name HP200 from Pall Specialty Materials Co. (Port Washington, N.Y.). The filter 185 may or may not be laminated to a backing, which provides additional support for the filter. This component provides a means of removal of residual particulates and enables retention of microbes contaminating the water source. Desirably, the porosity can be as low as a 10,000 molecular weight cutoff, sufficient to filter many viruses.

At the downstream end of the housing 110 is the housing outlet 130. The housing inlet 120 is covered by the housing inlet port cover 190. The housing outlet 130 is covered by the outlet port cover 195.

Preferably, water passing through the pack and exiting the housing conforms to the water quality standards by the AAMI for dyalysis water, and more preferably to the standards set forth in the U.S. Pharmacopoeia procedures for "Sterile Water for Injection."

Another suitable water purification pack is described at Col. 7, line 19 to Col. 8, line 24 of U.S. Pat. No. 5,725,777, entitled Reagent/Drug Cartridge, the disclosure of which is incorporated herein by reference.

Figure 4:
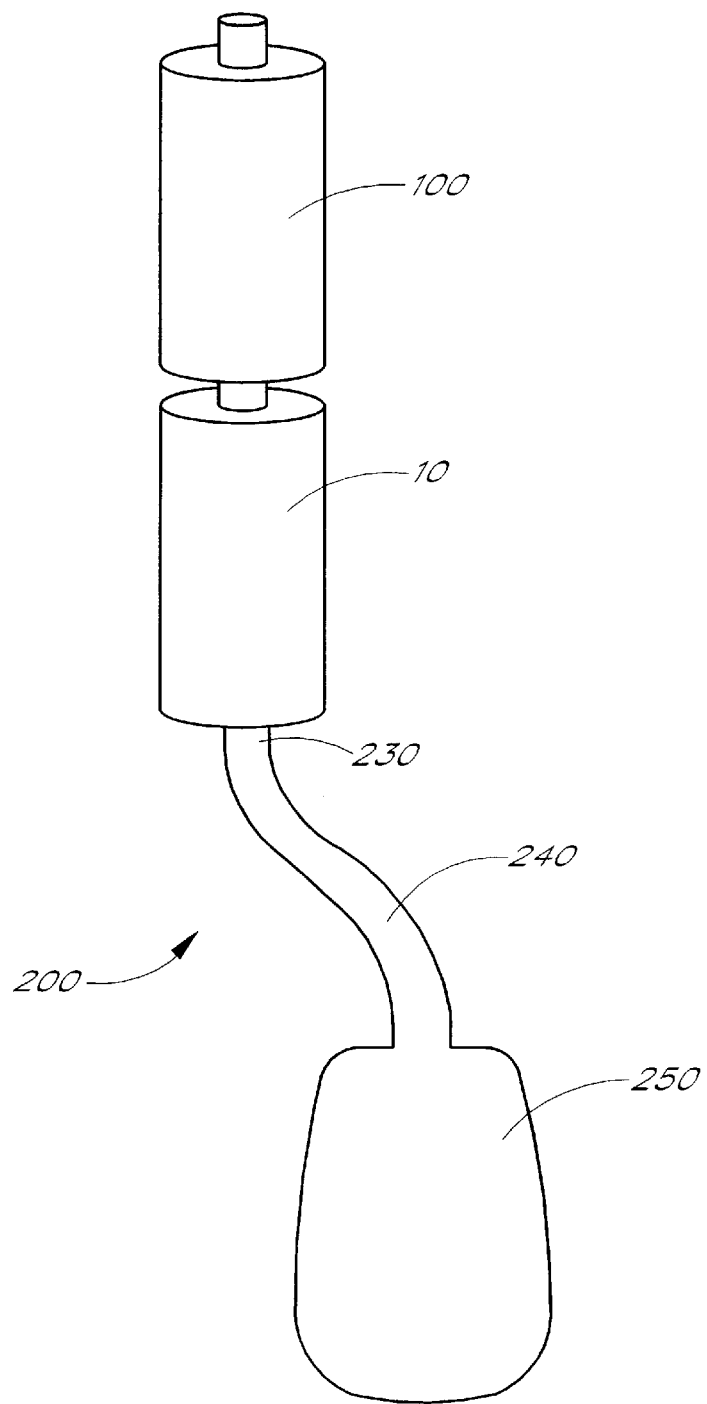
FIG. 4 is a schematic view of the combination of the hemodialysate delivery pack of FIGS. 1 and 2 with the water purification pack of FIG. 3 and a hemodialysate solution reservoir.

When combined as shown in FIG. 4, the water purification pack 100 and the hemodialysis cartridge 10 mate to each other. In addition, the hemodialysis housing outlet 230 attaches to a tubing 240 that connects the reagent cartridge 10 to any suitable collection reservoir 250.

Method of Operation

As set forth above, the illustrated device provides, in dry form, a complete formulation of the reagents required to produce a hemodialysis solution. These dry formulations typically contain reagents that form insoluble precipitates when exposed to each other for prolonged periods of time, in either dry or liquid forms. In the illustrated embodiment, sodium bicarbonate and calcium chloride are separately stored within the device housing. In use, the separate reagents are dissolved, just prior to use in hemodialysis, by providing diluent through the fluid axial pathway defined through the housing.

FIGS. 1 and 2 illustrate dissolution of dry reagent as diluent passes through the reagent beds. While illustrated cross-sectionally, it will be understood that the transparent or translucent housing materials will enable a user to observe dissolution of the reagent bed as solvent or diluent passes therethrough. Additionally, the user can observe whether insoluble precipitates are present within the reagent bed prior to employing the cartridge.

Prior to use, the inlet port 14 and the outlet port 16 (FIGS. 1 and 2) are covered by the inlet port cover 40 and the outlet port cover 42, respectively. With port covers 40 and 42 in place the interior contents of the housing remain sterile and are prevented from exposure to environmental humidity, which could potentially induce chemical changes in the reagent bed.

In operation, the inlet port cover 40 is removed (not shown) and the device is attached to a diluent source via the housing inlet 14. "Directly," as used herein, does not preclude use of intermediate tubing, etc., but rather refers to the fact that diluent can be purified on site immediately prior to solution formation or alternatively, diluent may be remotely produced and shipped. Diluent can comprise filtered and de-ionized water that is independently provided at the point of administration. Preferably, the diluent comprises water that is prepared for use by passage through the illustrated water purification pack 100 (see FIG. 3), most preferably connected upstream of the reagent cartridge 10 (see FIG. 4).

In preparation for use of the disclosed device, the outlet port cover 42 is removed (not shown) and the outlet port 16 is attached to the connection to a solution collection device, such as the reservoir 250 (FIG. 4). The illustrated reservoir 250 comprises one or more pliable, collection bags or dissolution systems for distribution of prepared hemodialysate solution.

Referring again to FIGS. 1 and 2, to achieve dissolution of the reagent beds 24 and 32, diluent is propelled into and through the delivery device 10 via external forces, such as active pumping or by gravitational force from a hanging water supply above the delivery device. Advantageously, the diluent can passively or gravimetrically (without additional forces other than gravity) pass through the pores of the upstream frit 18, the first compressive component 20 and the primary reagent bed upstream restraint 22. The diluent passes through the interstitial spaces between the particles constituting the primary reagent bed 24, resulting in the dissolution or eroding of the reagent bed 24. The dissolved reagents pass through the primary reagent bed downstream restraint 26. The porosity of this restraint 26 prevents passage of the dissolving particles until they are less than the pore size of the restraint.

Reagent solution then passes through the cells or lumen of the secondary compressive component 28, through the pores of the secondary reagent bed upstream restraint 30, and into the secondary reagent bed 32. Dissolution of the secondary reagent bed 32 follows. Solution including dissolved constituents of the primary reagent bed 24 and of the secondary reagent bed 32 mix and pass through the secondary reagent bed downstream restraint 34. As with the restraint 26, particles larger than the pores of this restraint 34 are retained until they are dissolved, or sufficiently reduced in size through dissolution, to pass through the restraint 34.

Solution, including constituents from both reagent beds 24, 32 passes through the cells or lumen of the third compressive component 36, the downstream frit 38 and the outlet 16. In the illustrated embodiment, the solution is suitable for hemodialysate. The thus-prepared hemodialysis solution passes through the reservoir tubing 240 (FIG. 4) and is preferably collected in a collection reservoir 250 (FIG. 4).

About 4 L of diluent ensures complete dissolution of the reagents of the illustrated amount (1212.5 g). Water can continue to run through the housing 12. Advantageously, however, 4 L of concentrated solution is then diluted to bring the solution to the appropriate concentration, which in the illustrated embodiment is accomplished by further diluting the concentrated solution with about 116 L of deionized or otherwise purified water.

In order to assure the maximum efficiency of the rate of dissolution, the individual particles within the reagent beds 24 and 32 are compressed together by axial pressure exerted by the compressive components 20, 28 and 36. Prior to dissolution these components 20, 28 and 36 are in partially or completely compressed, exerting maximal outward pressure axially, resulting in compression of the reagent beds 24 and 32 (FIG. 1). As the reagent beds 24 and 32 are dissolved, the compressive components expand to occupy space left by the dissolved reagents, continuing to exert axial pressure on the reagent beds 24 and 32 (FIG. 2).

For example, as the primary reagent bed 24 is dissolved, the first compression component 20 and second compression component 28 expand to further confine or compact the reagent bed 24 and facilitate uniform dissolution. Compacting in this manner prevents the formation of channels, which could create low resistance flow paths to bypass the reagents, thereby slowing the rate of dissolution. Similarly, as the secondary regent bed 32 dissolves, the second compression component 28 and third compression component 36 expand to further confine or compact the reagent bed 32 and facilitate uniform dissolution. It will be understood, of course, that only two compression components, such as the first and third components, can provide a similar function. Similarly, a single intermediate compression component, in the position of the illustrated second compression component 28, can accomplish this function, while advantageously also separating the incompatible reagent beds.

As previously noted, the size of the hemodialysis delivery pack can be varied to match the dry volume of the hemodialysate formulation. In the preferred embodiment, the contents of which are described in detail above, the device holds reagents sufficient to form about 4 L of concentrate, to be used, in turn, in making at least 100 L of hemodialysate solution, and in one embodiment 120 L of hemodialysate solution. Final volumes of solution of 110 L, 120 L, 130 L, 140 L, 150 L, 160 L, 170 L, 180 L, 190 L, 200 L, and more are contemplated. Fifty of the preferred devices can thus replace a 200 L drum of Preparation A concentrate and a 200 L drum of Preparation B concentrate.

Moreover, in the illustrated embodiment, the diluent can be purified on site at the time of solution formation. The water purification pack of FIG. 3 is attached upstream of the housing 110, as shown in FIG. 4, and a potable water supply is attached to the water purification pack housing inlet 120. Municipal water is under sufficient pressure (roughly 25 to 70 PSI) to propel itself through the water purification pack. Alternatively, a hand pump or other similar device can be supplied with a measured volume of water and used to pump the water therefrom into the purification pack 100.

Water passing through the inlet 120 of the purification pack 100 encounters the depth filter 140, where particulates larger than about 1 micron are filtered out. The water, purified of insoluble particulates by passage through the depth filter 140, then passes through the granular carbon bed 150, where residual organics such as endotoxins and additives such as chlorine, chloramine and trihalomethanes are absorbed. The water, purified of organic contaminants by passing through the carbon bed 150, then passes through the carbon bed restraint 160. Partially purified water then passes through the deionization resin bed 170. Dissociated ions and other charged particulates in solution bind to the resin bed 170. As deionized water exits the deionization bed 170, it encounters the deionization bed restraint 180. Water passing through the terminal filter 185 then exits the water purification housing 110 through the housing outlet 130. The terminal filter 185 can be optionally treated with a quaternary amine exchanger for binding residual endotoxins present in the filtrate.

The multiple filtration and chemical binding components of the water purification pack 100 thus ensure removal of particulate, ionic and organic contaminants from the diluent as it passes through the pack. Endotoxins, including organic matter such as cell walls from dead bacteria, can be particularly toxic. Highly purified diluent, sufficient to comply with the water quality standards of the U.S. pharmacopoeia for "sterile water for injection" is produced by filtration through the pack 100.

In the preferred embodiment of the invention, the water purification pack 100 of FIG. 3 is attached directly to the hemodialysis delivery pack. This component can be sized to match a varied volume of product water. In the preferred embodiment the water purification pack housing 110 comprises a cylinder about 11.5" in height and about 6" in diameter, capable of producing more than 150 liters of water meeting AAMI standards for water intended for subsequent production of hemodialysis solution. Accordingly, a single water purification pack (11.5" by 6"), in conjunction with a single drug reagent cartridge (13" by 2.5"), can produce 120 L of hemodialysis solution by the addition of available water.

Both these components work in concert to allow the intake of potable water and effluent of hemodialysis solution. Each of these components are free of water and are closed devices. Because of this characteristic, they are much more stable than water-or fluid-containing devices or systems. The single use nature of these devices minimizes the potential for contamination from prolonged and repeated use or improper sanitation following replacement of exhausted components, thus providing an additional safety factor over reusable systems. The cost of use is minimized by the decreased transportation and storage costs due to decreased volume and weight, decreased device costs due to use of less expensive materials of construction, and decreased unit costs due to extended expiration dating. Aseptic manufacture and sealing of inlets 12, 120 and outlets 16, 130 of the hemodialysis cartridge 10 and the water purification pack 100, respectively, assures that the device and attachment and the produced hemodialysis solution are aseptic.

In an alternative embodiment, a single reagent bed, with a portion of the reagents necessary for hemodialysis, can be similarly housed with a compression component. In this case, for example, the concentrate for Preparation A can be prepared by dissolution of the dry reagents though the housing, which is then mixed with a previously formed Preparation B, or vice versa. Incompatible reagents can be provided in separate cartridges, and Preparations A and B can be separately produced in accordance with the principles of the invention.

I claim:

1. A device for delivering dialysate solution from a single housing, comprising:
   a diluent inlet and a solution outlet, defining a fluid flow path therethrough;
   at least two discrete reagent beds within the housing along the fluid flow path comprising dry reagent in amounts and proportions sufficient for production of a complete dialysis solution, wherein one bed comprises a calcium salt and another bed comprises a bicarbonate; and
   at least one compression component positioned to exert pressure on the at least two discrete reagent beds.

2. The device of claim 1, wherein thedlysis solution is a hemodialysis solution.

3. The device of claim 1, wherein the compression component is expandable upon dissolution of the at least two reagent beds.

4. The device of claim 1, wherein said housing is from about 6 inches (15.24 cm) to about 24 inches (60.96 cm) in height and from about 1 inch (2.54 cm) to about 12 inches (30.48 cm) in diameter.

5. The device of claim 4, wherein the complete dialysis solution is a concentrate suitable to produce a final volume of at least 100 liters.

6. The device of claim 1, wherein the calcium salt is calcium chloride and the bicarbonate is sodium bicarbonate.

7. The device of claim 1, wherein the components of the separated reagent beds are present in a ratio of 1:1.2.

8. The device of claim 1, wherein said housing is configured to house multiple reagents suitable for the production of a hemodialysis solution by in situ dissolution of the reagents utilizing gravimetric diluent propulsion.

9. The device of claim 1, wherein the compression component comprises a compressible foam member.

10. The device of claim 1, wherein the compression component is positioned within a fluid flow path between the diluent inlet and the solution outlet, and comprises an open cell compressible foam member.

11. The device of claim 1, wherein the compression component comprises a coiled spring.

12. The device of claim 1, wherein the at least two reagent beds are compressed between an upstream compression component and a downstream compression component.

13. The device of claim 12, wherein the at least two reagent beds are confined between an upstream reagent restraint, positioned between the upstream compression component and the reagent bed, and a downstream reagent restraint, positioned between the downstream compression component and the reagent bed.

14. The device of claim 1, further comprising a water purification pack connected to the housing for purifying potable water to AAMI standards for water for a hemodialysis solution.

15. A system for providing hemodialysis solution, comprising:

a water purification pack; and a dry reagent module configured to connect downstream of the water purification pack, wherein said reagent module comprises a housing, a diluent inlet, a solution outlet, at least two separate reagent beds within the housing along a fluid flow path comprising dry reagent in amounts and proportions sufficient for production of a complete hemodialysis solution, wherein one bed comprises calcium chloride and another bed comprises sodium bicarbonate, and at least one compression component positioned to exert pressure on the at least two separate reagent beds.

16. The system of claim 15, wherein a porous, compressed, expandable component separates a first reagent bed from a second reagent bed, the first and second reagent beds comprising incompatible reagents.

17. The system of claim 15, wherein injection of potable water into the water purification pack results in a hemodialysis solution complying with AAMI standards.

18. The system of claim 17, wherein the injection does not require pressurization.

19. A device for storing and delivering dry reagents for medical fluids, comprising:

a single housing comprising a diluent inlet and a solution outlet, defining a fluid flow path therethrough;

at least two discrete reagent beds within the housing along the fluid flow path, wherein one bed comprises calcium chloride and other bed comprises sodium bicarbonate, and wherein the other bed is free of calcium chloride prior to use of the device; and the housing containing at least one compression component positioned to exert pressure on the at least two discrete reagent beds.

20. The device of claim 19, wherein the at least two discrete reagent beds are separated by a permeable internal restraint, wherein internal restraint permits the passage of dry reagents in solution upon introduction of a diluent through the diluent inlet.

21. The device of claim 19, wherein the compression component comprises an upstream spring element upstream of the at least two reagent beds and a downstream spring element downstream of the at least two reagent beds.

22. The device of claim 21, further comprising an intermediate spring element between the at least two reagent beds.

23. The device of claim 22, wherein each of the spring elements comprises a compressible foam member.

24. The device of claim 19, wherein the at least two reagent beds are separated by the compression component.

25. The device of claim 19, wherein the at least two reagent beds comprise reagents sufficient to produce a complete dialysis solution.

26. The device of claim 25, wherein the dialysis solution is a hemodialysate.

* * * * *

UNITED STATES PATENT AND TRADEMARK OFFICE
CERTIFICATE OF CORRECTION

PATENT NO. : 6,605,214 B1 Page 1 of 1
APPLICATION NO. : 09/518482
DATED : August 12, 2003
INVENTOR(S) : Michael A. Taylor It is certified that error appears in the above-identified patent and that said Letters Patent is hereby corrected as shown below:

In Col. 12, line 37, claim 2, please delete "thedlysis" and insert --the dialysis--

Signed and Sealed this

Twenty-eighth Day of August, 2007

JON W. DUDAS
*Director of the United States Patent and Trademark Office*